United States Patent
Niizeki et al.

(10) Patent No.: US 10,744,216 B2
(45) Date of Patent: Aug. 18, 2020

(54) FLUID STERILIZATION DEVICE

(71) Applicant: Nikkiso Co., Ltd, Tokyo (JP)

(72) Inventors: Shoichi Niizeki, Ishikawa (JP); Kenta Ura, Ishikawa (JP)

(73) Assignee: NIKKISO CO., LTD., Tokyo (JP)

( * ) Notice: Subject to any disclaimer, the term of this patent is extended or adjusted under 35 U.S.C. 154(b) by 0 days.

(21) Appl. No.: 16/261,776

(22) Filed: Jan. 30, 2019

(65) Prior Publication Data
US 2019/0240361 A1    Aug. 8, 2019

(30) Foreign Application Priority Data

Feb. 5, 2018 (JP) ................ 2018-018420

(51) Int. Cl.
*A61L 2/10* (2006.01)
*C02F 1/32* (2006.01)

(52) U.S. Cl.
CPC ............ *A61L 2/10* (2013.01); *C02F 1/325* (2013.01); *A61L 2202/11* (2013.01); *C02F 2201/3222* (2013.01); *C02F 2201/3227* (2013.01); *C02F 2201/3228* (2013.01); *C02F 2303/04* (2013.01)

(58) Field of Classification Search
CPC ........ A61L 2/10; A61L 2202/11; C02F 1/325; C02F 2201/3222; C02F 2201/3227; C02F 2201/3228; C02F 2303/04
See application file for complete search history.

(56) References Cited

U.S. PATENT DOCUMENTS

| | | | | |
|---|---|---|---|---|
| 2007/0114465 A1* | 5/2007 | Sajo | ............ | A61L 9/20 250/504 R |
| 2014/0042482 A1* | 2/2014 | Kim | ............ | H01L 33/58 257/99 |
| 2017/0144898 A1* | 5/2017 | Egner | ............ | C02F 1/325 |
| 2019/0142986 A1* | 5/2019 | Zhang | ............ | C02F 1/325 250/436 |

FOREIGN PATENT DOCUMENTS

JP    2012061413 A    3/2012

* cited by examiner

*Primary Examiner* — David E Smith
(74) *Attorney, Agent, or Firm* — Muncy, Geissler, Olds & Lowe, P.C.

(57) ABSTRACT

A fluid sterilization device includes: a processing flow passage in which a fluid subject to sterilization flows; a window member provided between a light source for irradiating the fluid in the processing flow passage with ultraviolet light and the processing flow passage, the window member including an incidence surface on which the ultraviolet light from the light source is incident and an exit surface from which the ultraviolet light exits toward the processing flow passage; and a heating body provided to be in contact with the incidence surface and adapted to heat the window member.

3 Claims, 7 Drawing Sheets

FLUID STERILIZATION DEVICE

RELATED APPLICATION

Priority is claimed to Japanese Patent Application No. 2018-018420, filed on Feb. 5, 2018, the entire content of which is incorporated herein by reference.

BACKGROUND OF THE INVENTION

1. Field of the Invention

The present invention relates to fluid sterilization devices and, more particularly, to a technology of sterilizing a fluid by irradiating the fluid with ultraviolet light.

2. Description of the Related Art

It is known that ultraviolet light has sterilization capability. Devices that radiate ultraviolet light are used for sterilization in medical and food processing fronts. Devices that sterilize a fluid such as water by continuously irradiating the fluid with ultraviolet light are also known. In a fluid sterilization device in which an ultraviolet lamp is used, a protective tube for transmitting ultraviolet light is provided between the flow passage and the ultraviolet lamp. To prevent dew condensation, a dried gas or a preheated gas is supplied to the interior of the protective tube.

It is preferred to efficiently prevent dew condensation on a window member for irradiating the fluid with ultraviolet light.

SUMMARY OF THE INVENTION

In this background, one illustrative purpose of the present invention is to provide a fluid sterilization device capable of efficiently preventing dew condensation on a window member.

A fluid sterilization device according to an embodiment includes: a processing flow passage in which a fluid subject to sterilization flows; a window member provided between a light source for irradiating the fluid in the processing flow passage with ultraviolet light and the processing flow passage, the window member including an incidence surface on which the ultraviolet light from the light source is incident and an exit surface from which the ultraviolet light exits toward the processing flow passage; and a heating body provided to be in contact with the incidence surface and adapted to heat the window member.

According to this embodiment, a heating body that is in contact with the incidence surface of the window member to heat the window member is provided. Therefore, the window member is heated efficiently and dew condensation is prevented.

The heating body may be provided to be in contact with the incidence surface both in a central region of the incidence surface and in an outer circumferential region of the incidence surface outside the central region.

The heating body may be thermally coupled to the light source.

The heating body may include a contact part that is in contact with the incidence surface and a connection part that extends from the light source to the contact part.

The heating body may include an electrically-heated wire provided on the incidence surface.

The heating body may further include an electrode part provided at an end of the electrically-heated wire on the incidence surface, and electric power is supplied via the electrode part.

The fluid sterilization device may further include a coating layer provided to coat the surface of the electrically-heated wire and made of a material having a higher ultraviolet reflectivity than the electrically-heated wire.

The fluid sterilization device may further include a coating layer provided to coat both the surface of the electrically-heated wire and the incidence surface and made of a material that transmits the ultraviolet light.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

A detailed description will be given of embodiments of the present invention with reference to the drawings. Like numerals are used in the description to denote like elements and a duplicate description is omitted as appropriate.

First Embodiment

Figure 1:
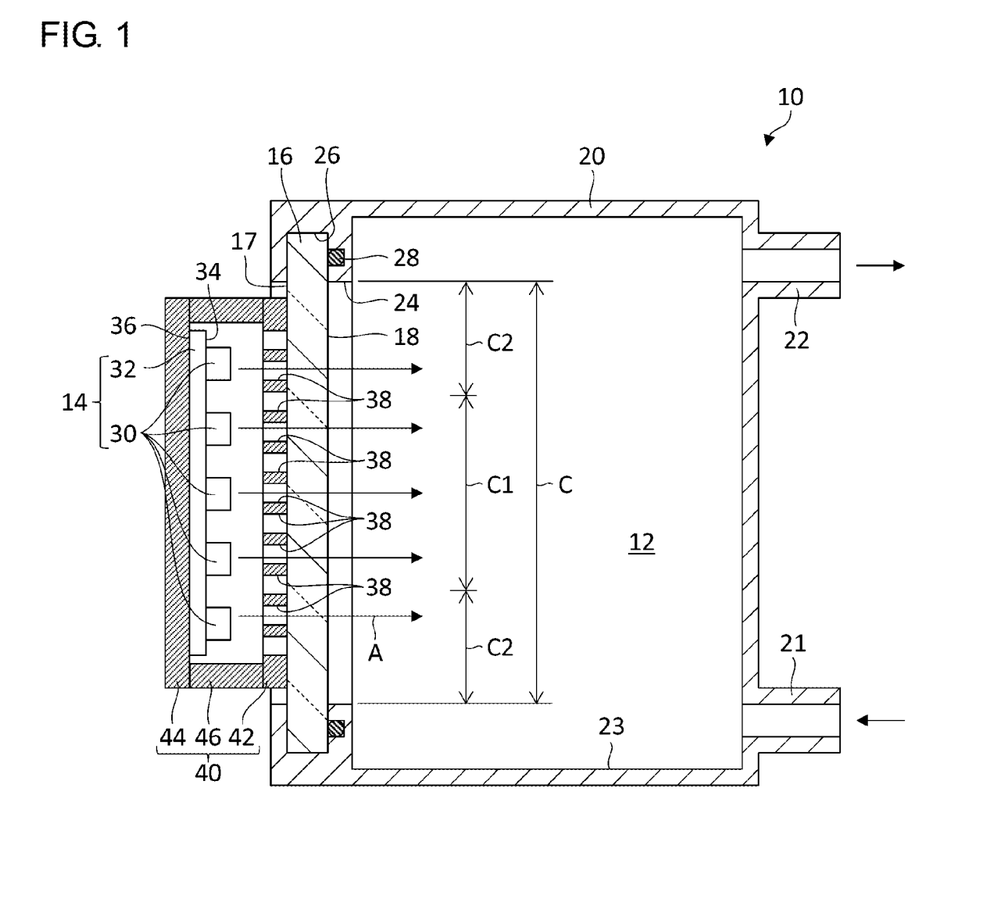
FIG. 1 is a cross-sectional view schematically showing a configuration of a fluid sterilization device according to a first embodiment.

FIG. 1 schematically shows a configuration of a fluid sterilization device 10 according to a first embodiment. The fluid sterilization device 10 includes a processing flow passage 12, a light source 14, a window member 16, and a heating body 40. The fluid sterilization device 10 is used to irradiate a fluid flowing in the processing flow passage 12 defined in a housing 20 with ultraviolet light A so as to sterilize the fluid. By providing the heating body 40 that is in contact with the window member 16, dew condensation on the window member 16 is prevented.

The housing 20 is a container that defines the processing flow passage 12. The housing 20 includes an inflow port 21, an outflow port 22, and an opening 24 provided with the window member 16. The material of the housing 20 is not limited to any particular one. It is preferred that at least an inner surface 23 of the housing 20 is made of a material having a high durability against ultraviolet light and a high ultraviolet reflectivity. For example, the inner surface 23 of the housing 20 is preferably made of a fluororesin like polytetrafluoroethylene (PTFE) or a metal material like aluminum (Al).

The light source 14 is provided outside the housing 20 and is arranged to radiate the ultraviolet light A toward the processing flow passage 12 in the housing 20 via the opening 24. The light source 14 includes a plurality of light emitting devices 30 and a substrate 32. The plurality of light emitting device 30 is arranged on a mounting surface 34 of the substrate 32. The light emitting device 30 is a so-called ultra violet-light emitting diode (UV-LED). It is preferred that the central wavelength or peak wavelength of the light emitting device 30 be included in a range of about 200 nm-350 nm and that the light emitting device 30 emit ultraviolet light near 260 nm-290 nm having a high sterilizing efficiency. Such an ultraviolet LED is exemplified by an aluminum gallium nitride (AlGaN) based LED.

The window member 16 is provided between the light source 14 and the processing flow passage 12 and transmits the ultraviolet light A from the light source 14 toward the processing flow passage 12. The window member 16 has an incidence surface 17 on which the ultraviolet light A from the light source 14 is incident and an exit surface 18 from which the ultraviolet light A exits toward the processing flow passage 12. It is preferred that the window member 16 be made of a material having a high ultraviolet transmittance and be configured to have an ultraviolet transmittance of 80% or higher. The window member 16 is made of a glass material such as quartz ($SiO_2$), sapphire ($Al_2O_3$), or an amorphous fluororesin.

The window member 16 is provided to block the opening 24 of the housing 20. For example, the window member 16 is laid in a recess 26 formed in the opening 24 of the housing 20. A sealing member 28 such as an O ring is provided between the window member 16 and the housing 20 to seal a gap between the window member 16 and the housing 20.

The heating body 40 is provided to be in contact with the window member 16 and prevents dew condensation on the window member 16 by heating the window member 16. The heating body 40 is provided to be in contact with a part of the incidence surface 17 of the window member 16 where dew condensation can occur. The heating body 40 is thermally coupled to the light source 14 and is configured to heat the window member 16 by using the heat generated by the light source 14. It is desired that the heating body 40 be made of a highly thermal conductive member. For example, the heating body 40 is made of a metal material such as copper (Cu) and aluminum (Al). In particular, aluminum can be used as a material for reflecting ultraviolet light as well and so is suitable as a material to make the heating body 40.

The heating body 40 includes a contact part 42, a base part 44, and a connection part 46. The contact part 42 is a part in contact with the window member 16 and is a plate member provided along the incidence surface 17 of the window member 16. The contact part 42 includes a plurality of through holes 38 for transmitting the ultraviolet light from the light source 14. Those portions of the contact part 42 that are provided with the through holes 38 are portions not in contact with the window member 16, and those portions not provided with the through holes 38 are portions in contact with the window member 16. The contact part 42 may be in direct contact with the incidence surface 17 of the window member 16 or may be in indirect contact with the incidence surface 17 via grease for increasing thermal conductivity. In this specification, "contact" of the heating body 40 encompasses both direct contact and indirect contact as described above.

It is preferred that the contact part 42 be in contact with the incidence surface 17 over the entirety of an opening region C of the window member 16 at portions excluding the through holes 38. The opening region C represents a region where the opening 24 of the housing 20 is formed and is a range in which the ultraviolet light A from the light source 14 can be transmitted. It is preferred that the contact part 42 be in contact with the incidence surface 17 both in a central region C1 of the incidence surface 17 of the window member 16 and in an outer circumferential region C2 outside the central region C1 of the incidence surface 17. There is no restriction to the boundary between the central region C1 and the outer circumferential region C2. For example, the boundary may be defined to bisect the area of the opening region C. By causing the contact part 42 to be in contact with both the central region C1 and the outer circumferential region C2 of the incidence surface 17, the window member 16 is heated more uniformly and local dew condensation is prevented. For example, the above-described provision prevents a situation in which dew is condensed in the central region C1 by causing the contact part 42 to be in contact only with the outer circumferential region C2.

The proportion of the opening region C of the window member 16 in contact with the contact part 42 is preferably not less than 30%, and more preferably not less than 50%. By ensuring that the proportion of the area of contact of the contact part 42 is not less than 30% or 50%, the window member 16 is suitably heated. Meanwhile, it is preferred to maintain the proportion of the area of contact of the contact part 42 to be not higher than 80% in order to prevent reduction in the amount of ultraviolet A of the light source 14 transmitted.

The base part 44 is a part that is in contact with the light source 14. The base part 44 is provided behind the light source 14 and is provided to be in contact with a back surface 36 of the substrate 32 opposite to the mounting surface 34. The base part 44 is provided to be in contact with at least a portion of the back surface 36 of the substrate 32. The base part 44 may be formed over the entirety of the back surface 36 of the substrate 32 in order to improve thermal connection with the light source 14.

The connection part 46 extends from the base part 44 to the contact part 42 and thermally couples the base part 44 and the contact part 42. For example, the connection part 46 is comprised of a columnar member of a cylindrical member extending in a direction of irradiation of the ultraviolet light A from the light source 14. The connection part 46 may include a heat pump. For example, the high-temperature part of the heat pipe may be fitted to the base part 44 and the low-temperature part of the heat pipe may be fitted to the contact part 42 in order to increase the efficiency of heat transfer from the base part 44 to the contact part 42.

Figure 2:
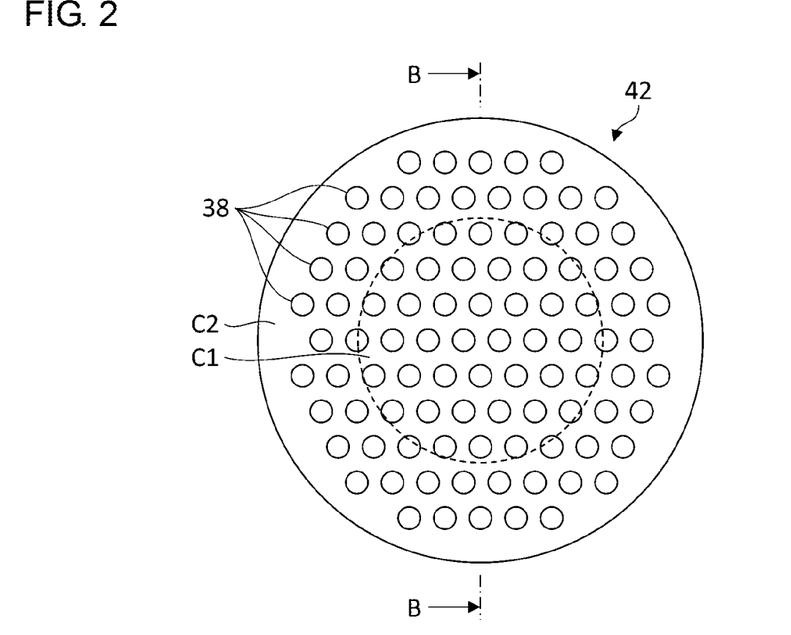
FIG. 2 is a plan view schematically showing a configuration of the contact part of FIG. 1.

FIG. 2 is a plan view schematically showing a configuration of the contact part 42 of FIG. 1. FIG. 1 corresponds to a B-B cross section of FIG. 2. The contact part 42 is disk-shaped to conform to the shape of the opening region C. The plurality of through holes 38 are circular openings and are arranged in a triangular grid pattern. The plurality of through holes 38 are arranged at uniform intervals both in the central region C1 and in the outer circumferential region C2. It should be noted that there is no restriction to the shape and arrangement of the through holes 38. The shape of the opening of the through hole 38 need not be circular and may be polygonal (e.g., triangular, rectangular, hexagonal). Alternatively, the opening may be shaped in an ellipse, sector, or annular sector. Still alternatively, the shape of the opening may be a combination of these. The through holes 38 may be arranged in a rectangular grid pattern or arranged irregularly. Alternatively, the plurality of through holes 38 may be arranged such that one of the through holes 38 is positioned to be in direct alignment with a respective one of the plurality of light emitting devices 30. There is no restriction to the size of the through hole 38, either. The size of the through hole 38 may be equal to, smaller than, or larger than the mounting area of each light emitting device 30.

Figure 3:
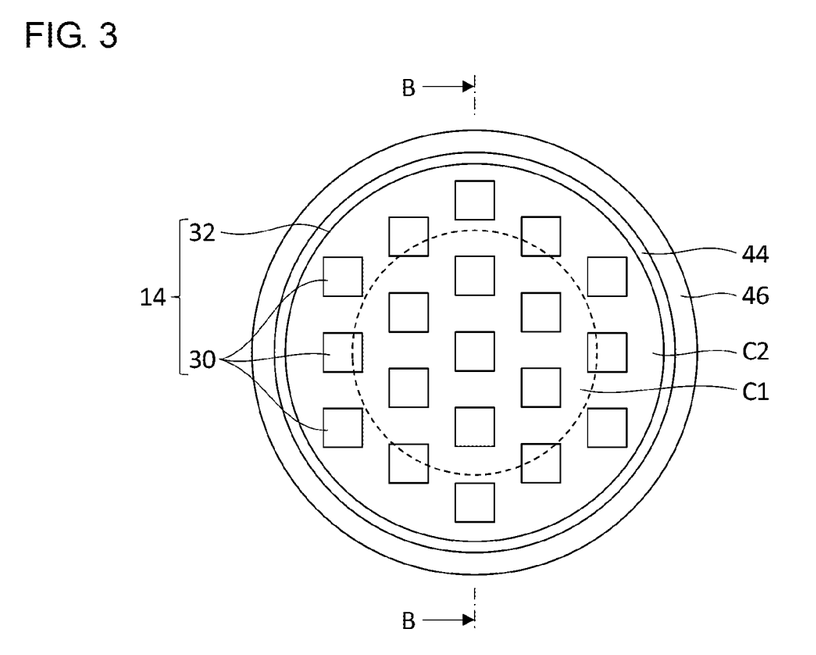
FIG. 3 is a plan view schematically showing a configuration of the light source and the connection part of FIG. 1.

FIG. 3 is a plan view schematically showing a configuration of the light source 14 and the connection part 46 of FIG. 1. FIG. 1 corresponds to a B-B cross section of FIG. 3. The substrate 32 is disk-shaped to conform to the shape of the opening region C, and the plurality of light emitting devices 30 are arranged on the substrate 32 in a triangular grid pattern. The connection part 46 is disk-shaped and is provided to surround the outer circumference of the light source 14. The connection part 46 may be provided continuously in the circumferential direction or provided discretely in the circumferential direction. The connection part 46 may be comprised of a plurality of heat pipes arranged in the circumferential direction at intervals.

A description will now be given of the operation of the fluid sterilization device 10. The fluid subject to the sterilization (e.g., water) flows into the housing 20 via the inflow port 21, and the fluid flows in the processing flow passage 12. The light source 14 is lighted, and the fluid flowing in the processing flow passage 12 is irradiated with the ultraviolet light A from the light source 14. The fluid irradiated with the ultraviolet light A in the processing flow passage 12 is discharged from the outflow port 22. The heat generated by the light source 14 is transferred to the heating body 40, and the heating body 40 heats the window member 16 by using the heat from the light source 14. Since the window member 16 is heated by the heating body 40, dew condensation that may occur on the incidence surface 17 of the window member 16 is prevented even when the temperature of the fluid subject to treatment is low.

In accordance with this embodiment, troubles that could occur in the light emitting devices 30 or the wiring in the substrate 32 due to the moisture produced by dew condensation are prevented by preventing dew condensation on the incidence surface 17 of the window member 16. Further, the embodiment is capable of preventing the transmittance of the window member 16 from being lowered due to drops of water attached to the incidence surface 17 of the window member 16 to result in lowered sterilization performance. In this way, the fluid sterilization device 10 can be operated in a stable manner.

According to this embodiment, the heating body 40 that is in contact with the incidence surface 17 of the window member 16 is used to heat the window member 16 so that the heating mechanism is simplified and the thermal efficiency is increased as compared to the scheme of blowing hot air for heating. Because the heat generated by the light source 14 is used, the power consumption in the device as a whole is reduced as compared to the case of providing a heat generating mechanism such as a heater.

Figure 4:
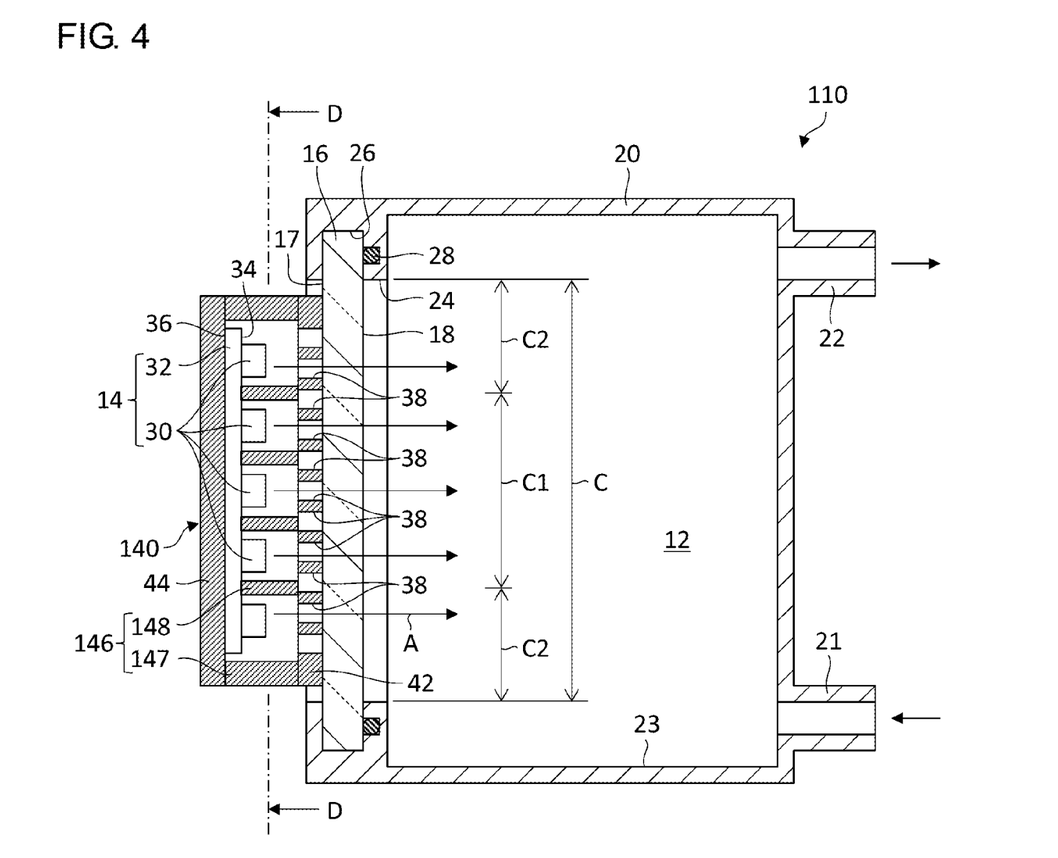
FIG. 4 is a cross-sectional view schematically showing a configuration of a fluid sterilization device according to a variation.

FIG. 4 is a cross-sectional view schematically showing a configuration of a fluid sterilization device 110 according to a variation. The variation differs from the aforementioned embodiment in that a second connection part 148 extending from the light source 14 to the contact part 42 is additionally provided. The following description of the variation highlights the difference from the embodiment described above. A description of features that are common is omitted as appropriate.

The fluid sterilization device 110 includes a processing flow passage 12, a light source 14, a window member 16, and a heating body 140. The heating body 40 includes a contact part 42, a base part 44, and a connection part 146. The contact part 42 and the base part 44 are configured in a manner similar to that of the embodiment described above. The connection part 146 includes a first connection part 147 that extends from the base part 44 to the contact part 42 and a second connection part 148 that extends from the light source 14 to the contact part 42. The first connection part 147 is configured in a manner similar to that of the connection part 46 according to the embodiment described above. The second connection part 148 is provided between the plurality of light emitting devices 30 and is in contact with the mounting surface 34 of the substrate 32.

Figure 5:
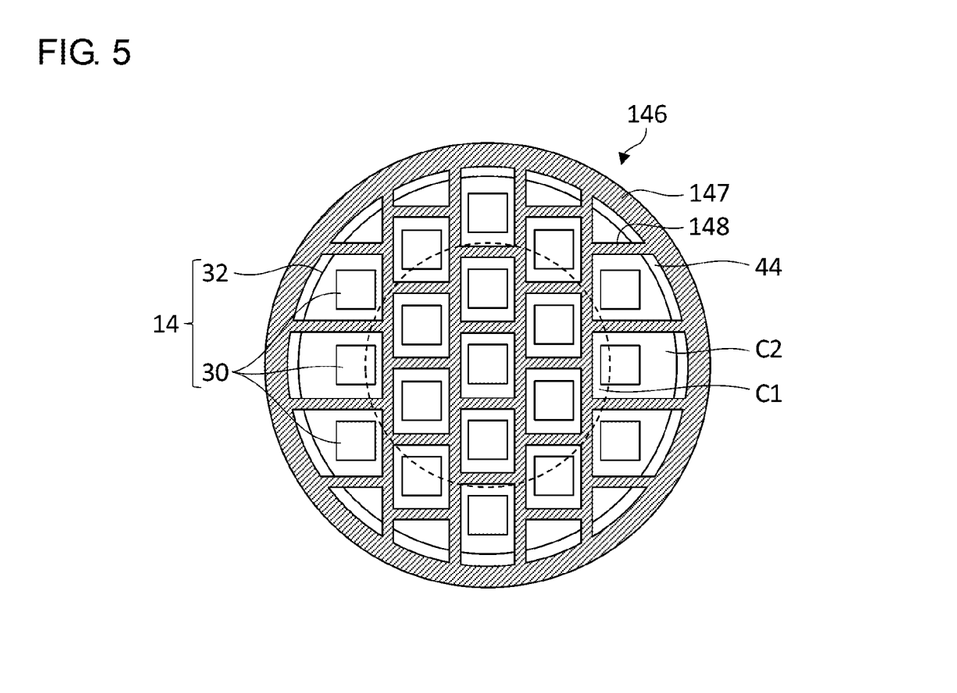
FIG. 5 is a cross-sectional view schematically showing a configuration of the connection part of FIG. 4.

FIG. 5 is a cross-sectional view schematically showing a configuration of the connection part 146 of FIG. 4 and shows a D-D cross section of FIG. 4. As illustrated, the first connection part 147 is formed in a cylindrical shape so as to surround the outer circumference of the light source 14, and the second connection part 148 is formed in a grid pattern so as to partition between the plurality of light emitting devices 30. For example, the second connection part 148 is provided between adjacent light emitting devices 30. The second connection part 148 is provided along each of the four sides of each rectangular light emitting device 30 and is provided to define small rectangular rooms in which the respective light emitting devices 30 are accommodated. The second connection part 148 may be provided in an arc pattern. For example, the small rooms accommodating the respective light emitting devices 30 may have a shape of a circle or a sector. The second connection part 148 may not necessarily be provided to partition each one of the light emitting devices 30. For example, the second connection part 148 may be provided such that a certain number of (a plurality of) (e.g., two, three, or four) light emitting devices 30 are accommodated in a small room partitioned by the second connection part 148.

According to this variation, thermal connection between the light source 14 and the contact part 42 is improved and the incidence surface 17 of the window member 16 is heated more efficiently, by providing the second connection part 148 between the plurality of light emitting devices 30. By forming the second connection part 148 using a material having a high ultraviolet reflectivity like aluminum (Al), the ultraviolet light output from the light emitting devices 30 are guided toward the window member 16 by being reflected by the surface of the second connection part 148. This makes the intensity distribution of the ultraviolet light incident on the window member 16 uniform and increases the efficiency of irradiating the fluid with ultraviolet light.

Second Embodiment

Figure 6:
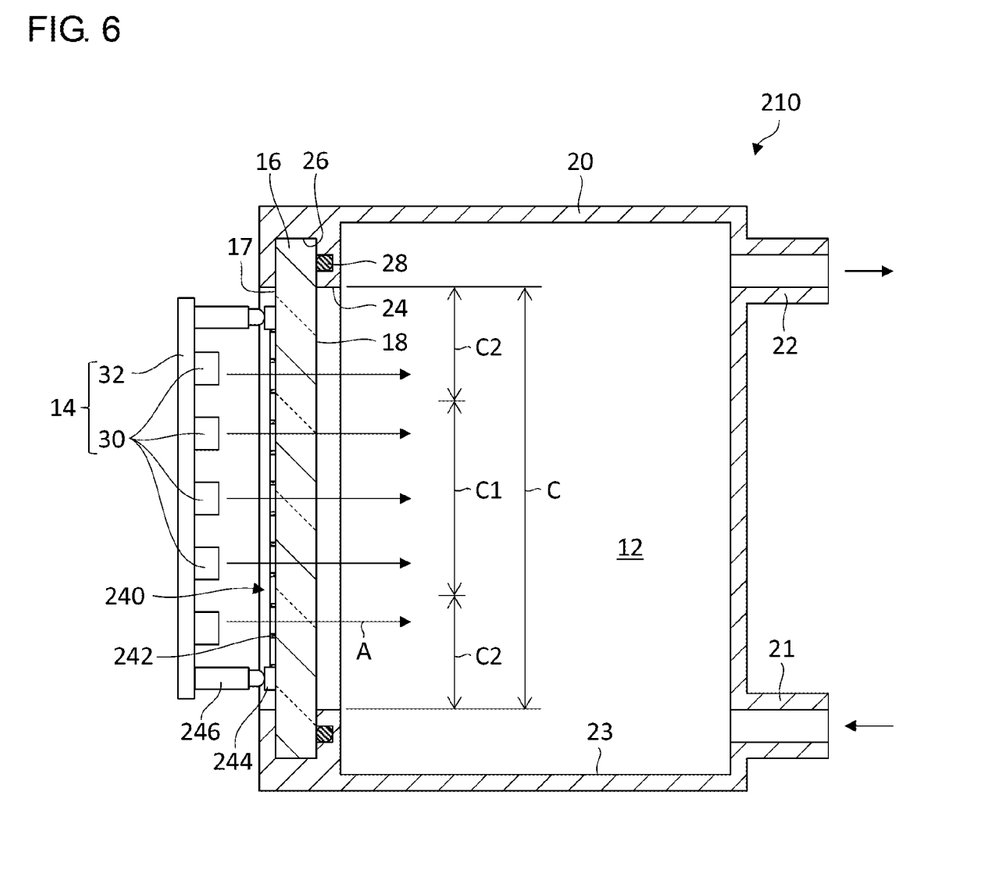
FIG. 6 is a cross-sectional view schematically showing a configuration of a fluid sterilization device according to a second embodiment.

FIG. 6 is a cross-sectional view schematically showing a configuration of a fluid sterilization device 210 according to a second embodiment. According to the embodiment, the window member 16 is not heated by using the heat of the light source 14, but the window member 16 is heated by providing a heat generator such as an electrically-heated wire on the incidence surface 17 of the window member 16. The following description of the variation highlights the difference from the embodiment described above. A description of features that are common is omitted as appropriate.

The fluid sterilization device 210 includes a processing flow passage 12, a light source 14, a window member 16, and a heating body 240. The heating body 240 includes an electrically-heated wire 242 and an electrode part 244. The electrically-heated wire 242 is provided on the incidence surface 17 of the window member 16 and is provided both in the central region C1 and the outer circumferential region C2 of the incidence surface 17. The electrode part 244 is provided on the incidence surface 17 of the window member 16 and is provided at the end of the electrically-heated wire 142. The electric power of the electrically-heated wire 242 is supplied from the substrate 32 via a connection part 246 extending from the substrate 32 to the electrode part 244.

Figure 7:
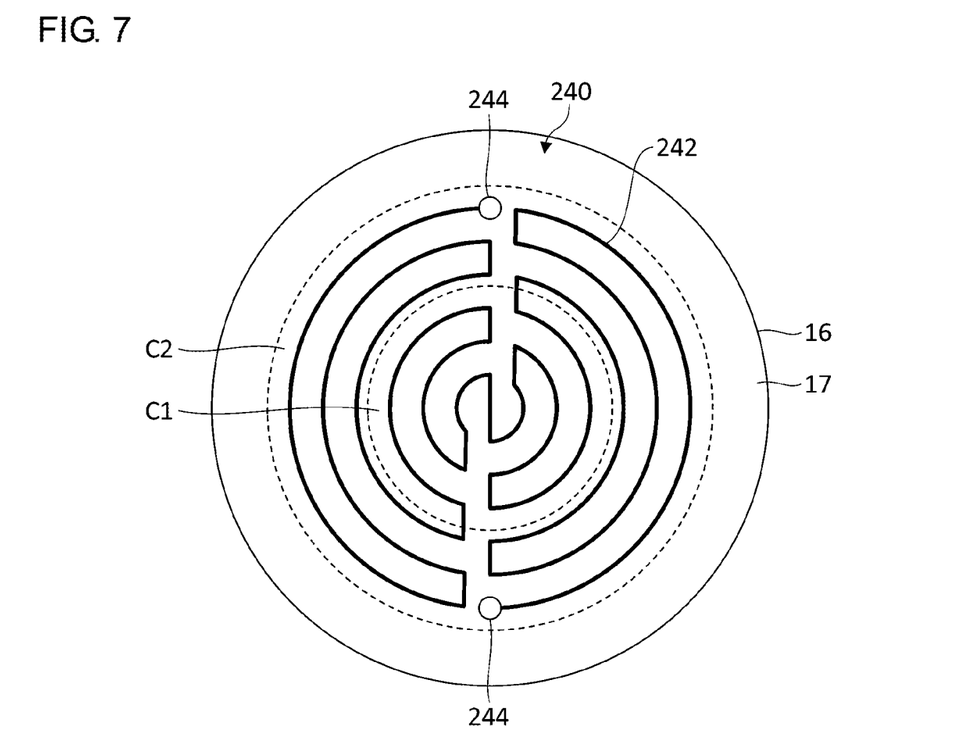
FIG. 7 is a plan view schematically showing a configuration of the heating body of FIG. 6.

FIG. 7 is a plan view schematically showing a configuration of the heating body 240 of FIG. 6. The electrically-heated wire 242 is provided in a spiral pattern both in the central region C1 and the outer circumferential region C2 of the incidence surface 17. The electrode part 244 is provided at both ends of the electrically-heated wire 242. For example, the electrode part 244 is provided in the outer circumferential region C2 of the incidence surface 17. The electrode part 244 may be provided in a region outside the central region C1 or the outer circumferential region C2. The electrically-heated wire 242 and the electrode part 244 can be formed by depositing a conducting film on the incidence surface 17 or adhesively attaching a conductive film sheet on the incidence surface 17.

A coating layer made of a material having a high ultraviolet reflectivity like aluminum (Al) may be provided on the surface of the electrically-heated wire 242. By providing a coating layer of high reflectivity, the ultraviolet light absorbed by the electrically-heated wire 242 is reflected and guided toward the processing flow passage 12, and the efficiency of irradiating the fluid with ultraviolet light is increased. For electrical insulation from the electrically-heated wire 242, an electrical insulation layer may be provided between the electrically-heated wire 242 and the coating layer.

According to this embodiment, the window member 16 is heated by using the electrically-heated wire 242 provided on the incidence surface 17 of the window member 16, thereby preventing dew condensation on the window member 16. In this embodiment, as in the foregoing embodiment, the window member 16 is heated by using the heating body 240 that is in contact with the incidence surface 17 of the window member 16 so that the heating mechanism is simplified and the thermal efficiency is increased as compared to the scheme of blowing hot air for heating.

Figure 8:
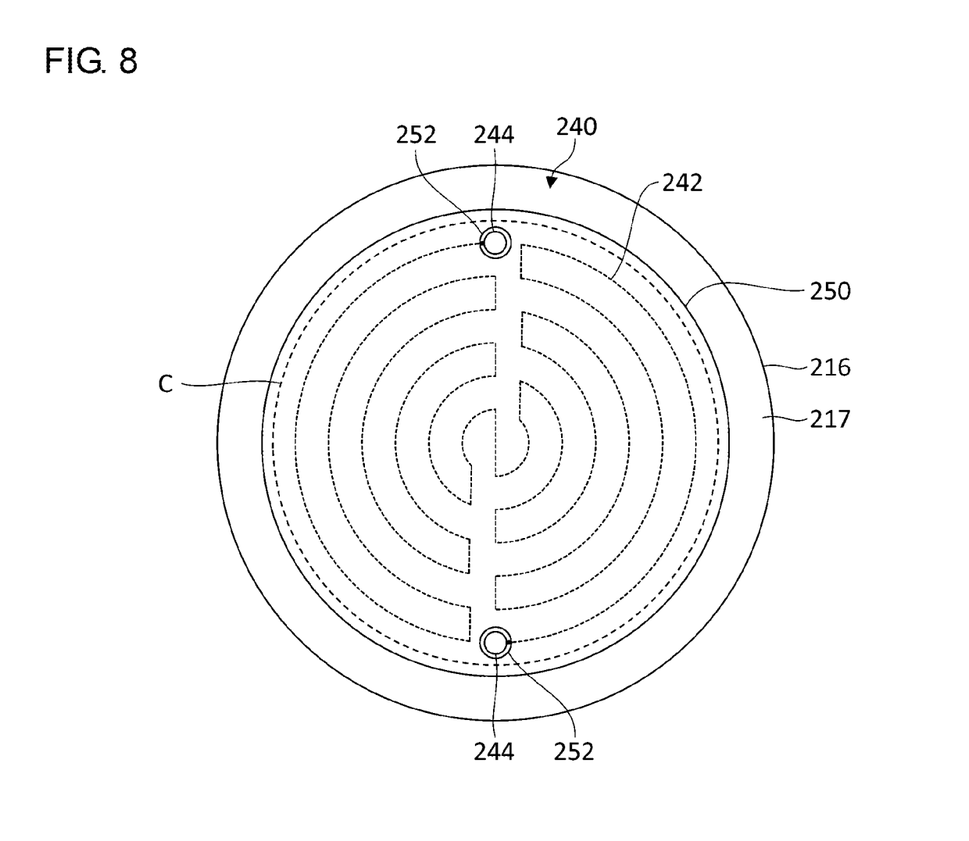
FIG. 8 is a plan view schematically showing a configuration of a window member according to a variation.

FIG. 8 is a plan view schematically showing a configuration of a window member 216 according to a variation. The window member 216 according to this variation differs from that of the embodiments described above in that a coating layer 250 is further provided on the entirety of the incidence surface 217 of the window member 216. The coating layer 250 has an electrode part opening 252 provided at a position corresponding to the electrode part 244 of the heating body 240. The coating layer 250 is provided to coat the entirety of the opening region C of an incidence surface 217 except for the electrode part opening 252 and to coat the entirety of the electrically-heated wire 242 provided on the incidence surface 217.

It is preferred that the coating layer 250 be made of an electrically insulative and damp-proof material and be made of a material having a high ultraviolet transmittance. For example, the coating layer 250 may be made of an inorganic material such as silicon oxide ($SiO_2$) and magnesium fluoride ($MgF_2$) or an organic material such as an amorphous fluororesin and a silicone resin. By providing the coating layer 250 on the entirety of the opening region C, the moisture produced by dew condensation is prevented from coming into contact with the electrically-heated wire 242, thereby preventing the electrically-heated wire 242 from being short-circuited in part or being degraded by the moisture.

Described above is an explanation based on an exemplary embodiment. The embodiment is intended to be illustrative only and it will be understood by those skilled in the art that various design changes are possible and various modifications are possible and that such modifications are also within the scope of the present invention.

The fluid sterilization device according to the embodiments and variations described above is described as a device for irradiating a fluid such water with ultraviolet light so as to sterilize the fluid. In one variation, the inventive sterilization device may be used for a purification process that decomposes organic substance included in a fluid by using ultraviolet irradiation.

It should be understood that the invention is not limited to the above-described embodiment but may be modified into various forms on the basis of the spirit of the invention. Additionally, the modifications are included in the scope of the invention.

What is claimed is:

1. A fluid sterilization device comprising:
a processing flow passage in which a fluid subject to sterilization flows;
a window member provided between a light source for irradiating the fluid in the processing flow passage with ultraviolet light and the processing flow passage, the window member including an incidence surface on which the ultraviolet light from the light source is incident and an exit surface from which the ultraviolet light exits toward the processing flow passage; and
a thermally conductive heating body comprising a contact part and a connection part, wherein the heating body is adapted to heat the window member by transferring heat generated by the light source to the window member through the contact part and the connection part, wherein the contact part that is in contact with the incidence surface and the connection part extends from the light source to the contact part wherein the contact part is provided to be in contact with the incidence surface both in a central region of the incidence surface and in an outer circumferential region of the incidence surface outside the central region.

2. A fluid sterilization device comprising:
a processing flow passage in which a fluid subject to sterilization flows;
a window member provided between a light source for irradiating the fluid in the processing flow passage with ultraviolet light and the processing flow passage, the window member including an incidence surface on which the ultraviolet light from the light source is incident and an exit surface from which the ultraviolet light exits toward the processing flow passage;
an electrically-heated wire provided on the incidence surface; and
a coating layer provided to coat both a surface of the electrically-heated wire and the incidence surface, wherein the coating layer is made of a material that is damp-proof and transmits the ultraviolet light.

3. The fluid sterilization device according to claim 2, wherein
the coating layer does not cover an electrode part provided at an end of the electrically-heated wire on the incidence surface, and electric power is supplied to the electrically-heated wire via the electrode part.

* * * * *